US012773256B2

(12) United States Patent
Dunning et al.

(10) Patent No.: US 12,773,256 B2
(45) Date of Patent: Oct. 27, 2026

(54) LARGE AREA HEMOSTASIS WITH VESSEL SEALING

(71) Applicant: Medtronic Advanced Energy LLC, Minnneapolis, MN (US)

(72) Inventors: James E. Dunning, Boulder, CO (US); Brian Lane, Fridley, MN (US); Erin E. Wehrly, Boulder, CO (US); Prakash Manley, Arvada, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 801 days.

(21) Appl. No.: 17/702,133

(22) Filed: Mar. 23, 2022

(65) Prior Publication Data

US 2023/0139073 A1 May 4, 2023

Related U.S. Application Data

(60) Provisional application No. 63/274,454, filed on Nov. 1, 2021.

(51) Int. Cl.
*A61B 18/14* (2006.01)
*A61B 17/00* (2006.01)
(Continued)

(52) U.S. Cl.
CPC .................... *A61B 18/1442* (2013.01); *A61B 2017/00438* (2013.01); *A61B 2018/00077* (2013.01);
(Continued)

(58) Field of Classification Search
CPC ........... A61B 18/1442; A61B 18/1445; A61B 2018/00589; A61B 2018/00077;
(Continued)

(56) References Cited

U.S. PATENT DOCUMENTS 5,611,813 A * 3/1997 Lichtman .......... A61B 18/1445 606/174
6,059,776 A 5/2000 Gatto
(Continued)

FOREIGN PATENT DOCUMENTS

EP 1 767 163 A1 3/2007
EP 2 275 050 A1 1/2011
(Continued)

OTHER PUBLICATIONS

International Search Report and Written Opinion from PCT Application PCT/IB2022/060503 dated Feb. 1, 2023, 15pgs.
(Continued)

*Primary Examiner* — Joseph A Stoklosa
*Assistant Examiner* — Marina Delaney Templeton
(74) *Attorney, Agent, or Firm* — Husch Blackwell LLP

(57) ABSTRACT

A multifunction surgical instrument having a low-profile configuration to deliver both small vessel sealing through a bipolar clamping mechanism and transcollation sealing of diffused bleeding in a broad tissue plane, the multifunction surgical instrument including a first jaw and a second jaw configured to transition between an open position and a closed position to serve as a clamp for sealing of tissue, and a disposable electrode portion comprising a first conductive surface positioned in proximity to the first jaw and a second conductive surface positioned in proximity to the second jaw, the first and second conductive surfaces configured to emit a high-frequency alternating current, and two or more electrodes and at least one saline port, wherein the two or more electrodes in the at least one saline port cooperate to affect transcollation sealing of diffused bleeding within a broad tissue plane.

18 Claims, 11 Drawing Sheets

(51) Int. Cl.

*A61B 18/00* (2006.01)
*A61B 18/12* (2006.01)
*A61B 90/30* (2016.01)

(52) U.S. Cl.

CPC ............... *A61B 2018/00589* (2013.01); *A61B 2018/0063* (2013.01); *A61B 2018/126* (2013.01); *A61B 2018/1455* (2013.01); *A61B 2090/309* (2016.02); *A61B 2218/002* (2013.01)

(58) Field of Classification Search

CPC ...... A61B 2018/0063; A61B 2018/126; A61B 2018/1455; A61B 2018/00607; A61B 2018/00922; A61B 2018/00916; A61B 2018/00994; A61B 2018/00702; A61B 2017/00438; A61B 2017/00017; A61B 218/002; A61B 2090/065; A61B 2090/064

See application file for complete search history.

(56) References Cited

U.S. PATENT DOCUMENTS

| | | | | |
|---|---|---|---|---|
| 6,652,521 | B2 * | 11/2003 | Schulze ............. | A61B 18/1445 606/50 |
| 7,150,097 | B2 * | 12/2006 | Sremcich ........... | A61B 18/1445 29/857 |
| 10,631,914 | B2 | 4/2020 | Sartor et al. | |
| 2012/0116391 | A1 * | 5/2012 | Houser .................. | A61B 34/76 606/1 |
| 2014/0094795 | A1 * | 4/2014 | Keller ................ | A61B 18/1445 606/34 |
| 2015/0066026 | A1 * | 3/2015 | Hart ....................... | A61B 34/76 606/46 |
| 2015/0080880 | A1 * | 3/2015 | Sartor ................ | A61B 18/1445 606/51 |
| 2015/0141981 | A1 * | 5/2015 | Price .................. | A61B 18/1445 606/38 |
| 2017/0105789 | A1 * | 4/2017 | Boudreaux ........ | A61B 18/1445 |
| 2017/0238991 | A1 * | 8/2017 | Worrell .................. | H05K 1/034 |
| 2019/0206555 | A1 * | 7/2019 | Morgan ................. | G16H 40/20 |
| 2019/0365457 | A1 * | 12/2019 | Joseph ............... | A61B 18/1206 |
| 2020/0008860 | A1 * | 1/2020 | Sims .................. | A61B 18/1445 |
| 2020/0107845 | A1 * | 4/2020 | Kabala ............. | A61B 17/22031 |
| 2020/0107876 | A1 | 4/2020 | Allen et al. | |
| 2022/0395314 | A1 | 12/2022 | Segit et al. | |

FOREIGN PATENT DOCUMENTS

| | | | |
|---|---|---|---|
| EP | 2 428 177 | A1 | 3/2012 |
| EP | 3 581 125 | A1 | 12/2019 |
| WO | WO 2016/088017 | A1 | 6/2016 |
| WO | WO 2017/024124 | A1 | 2/2017 |

OTHER PUBLICATIONS

Application and file history for U.S. Appl. No. 17/348,690, filed Jun. 15, 2021, inventors Segit et al.

https://www.youtube.com/watch?v=QmgKEsiLymM, Bipolar Vessel Sealing and Dissection Devices, uploaded on Apr. 16, 2017, Twomey Consulting, 3:25 minutes, 480p, Bipolar vessel sealing and dissection devices use advanced radiofrequency energy to seal blood vessels and other tissue structures. These devices are used in open, laparoscopic, and thoracoscopic surgery.

https://www.youtube.com/watch?v=26cMx8LWk_A, How Ligasure Works?, uploaded on Mar. 3, 2019, Dr. R.K. Mishra, 15:57 minutes, 480p. This video demonstrates how Ligasure works presented by Dr. R K Mishra. Ligasure is a tissue response generator. Across the range of products and procedures, LigaSure also called a vessel sealer is a technology that delivers a unique combination of pressure and energy to create a consistent seal with each application. Ligasure provides a combination of pressure and energy to create vessel fusion. Permanently fuses vessels up to and including 7 mm in diameter and tissue bundles without dissection or isolation. The average seal cycle is 2 to 4 seconds. Ligasure seals withstand three times normal systolic blood pressure. Feedback-controlled response system automatically discontinues energy delivery when the seal cycle is complete, eliminating the guesswork.

https://www.youtube.com/watch?v=o3SXfg2A8-U, Sanus Ithalat, uploaded Nov. 21, 2018, 3:12 minutes, 480p, aquamantys transcollation animation video.

* cited by examiner

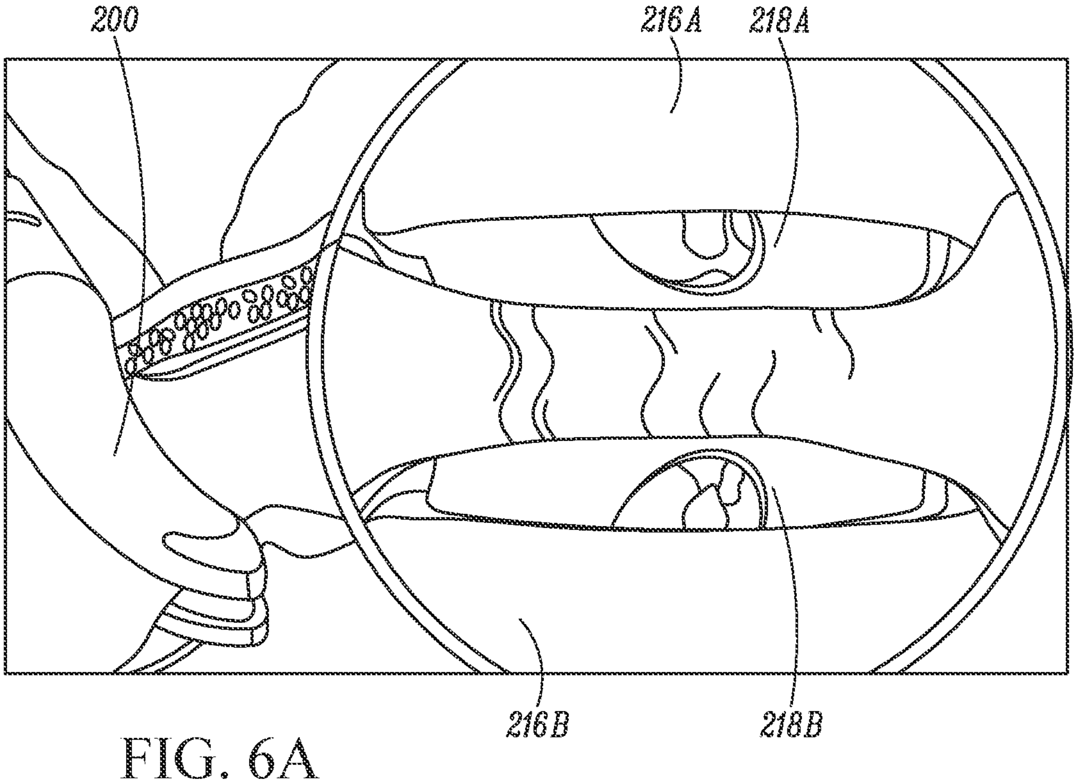
FIG. 6A
FIG. 6B
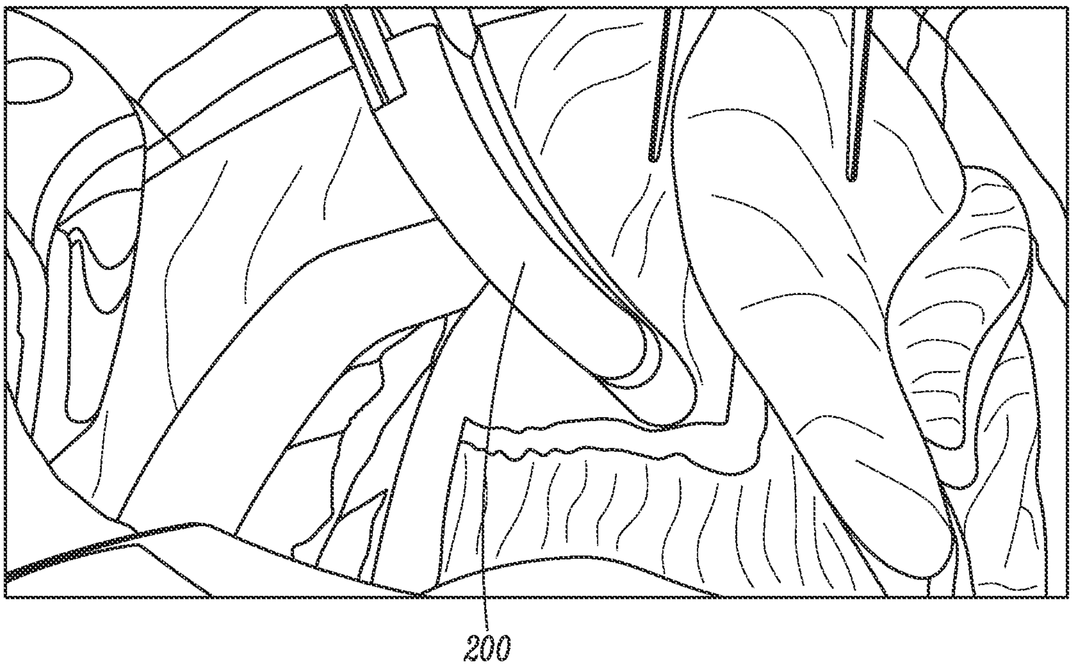
FIG. 6C

LARGE AREA HEMOSTASIS WITH VESSEL SEALING

CROSS-REFERENCE TO RELATED APPLICATIONS

The present application claims the benefit of U.S. Provisional Application No. 63/274,454, filed Nov. 1, 2021, the contents of which are fully incorporated herein by reference.

TECHNICAL FIELD

The present technology is generally related to the field of surgical instruments. In particular, the disclosure relates to a multi-function transection device for use in open surgical procedures.

BACKGROUND

Bipolar vessel sealing and dissection devices use advanced radiofrequency to seal blood vessels and other tissue structures, and are commonly used in open, laparoscopic, and thoracoscopic procedures. These devices are often used for sealing and dividing blood vessels and other tissue structures through a combination of radiofrequency energy and pressure. Common procedures in which bipolar vessel sealing and dissection devices are used include hysterectomies, colectomies, splenectomies, gastrectomies, pancreatectomies, nephrectomies, adhesiolysis and endometriosis resection, among others.

With reference to FIG. 1, a typical bipolar vessel sealing device 100 is depicted in accordance with the prior art. The device 100 can include a pair of jaws 102A/B configured to hold tissue layers together like a clamp. Radiofrequency energy from a generator 104 is delivered to the tissue through conductive surfaces 106A/B on the jaws 102A/B; specifically, the conductive surfaces 106A/B can include two electrical poles, hence the term "bipolar." One example of such a device is the Ligasure® Impact™, manufactured and sold by Medtronic, plc.

In operation, tissue is placed between the jaws 102A/B. A clinician or user then squeezes a lever 108 to close the jaws 102A/B and presses a trigger 110 to activate the generator 104. Thereafter, a high-frequency alternating current from the generator 104 causes hydrated tissue clamped between the jaws 102A/B to heat up, which in turn causes collagen and elastin molecules within the tissue to melt and fuse back together thereby creating a seal. Accordingly, bipolar vessel sealing and dissection devices are well adapted at sealing and dividing tissues that can be positioned between the pair of jaws 102A/B.

For treatment of broad plane tissues (e.g., tissue that is not readily positioned between the pair of jaws 102A/B), medical personnel may turn to other types of devices, for example, a device which employs transcoalition or another type of broad plane tissue sealing technology. Unlike bipolar vessel sealing, transcoalition enables pretreatment of tissue prior to dissection, as well as the treatment of blood vessels that have retracted into a surrounding broad plane of tissue.

With reference to FIG. 2, a transcoalition sealing device 150 is depicted in accordance with the prior art. As depicted, the transcoalition sealing device 150 can include a pair of electrodes 152A/B and a saline port 154 configured to deliver a combination of radiofrequency energy and saline to the tissue. In particular, the saline is delivered at a rate matched to the power setting on the system pump generator

156. One example of such a device is the Aquamantys™ Sealer, manufactured and sold by Medtronic, plc.

In operation, transcoalition can be affected through a painting motion of the device 150 upon the tissue to be treated while pressing an activation button 158 to seal broad tissue planes or spot treat bleeding vessels up to about 1 mm in diameter. Unlike traditional electrocautery, transcoalition provides low temperature hemostasis, with temperatures generally at or below 100° C., thereby reducing the likelihood of burning char or smoke.

Speed is a critical factor for reducing the amount of time patients are held under anesthesia, and for reducing the cost of time in the operating room. Bipolar vessel sealing devices 100 and transcoalition devices 150 have each proven extremely effective in this respect, particularly in comparison to manual dissection with sutures or electrocautery. Specifically, these devices have been found to reduce procedure times while reducing blood loss, hospital stays, recovery time, and postoperative pain. Moreover, these devices seal tissue without leaving any foreign objects, like sutures, staples or clips, in the body.

Although such devices have proven to work extremely well, the large handle associated with these devices, which is often in the form of a pistol grip, can present visibility issues, as well as generally having an unnatural feeling to an experienced surgeon who may have previously relied on a hemostat or scalpel. Moreover, the use of multiple tools during a surgical procedure increases the complexity and time required for the completion of a surgical procedure. The present disclosure addresses these concerns.

SUMMARY OF THE DISCLOSURE

The techniques of this disclosure generally relate to a multifunction surgical instrument having a low-profile, ring handle configured to deliver both vessel dissection and sealing through a bipolar clamping mechanism and a combination of bipolar radiofrequency energy and saline to provide hemostatic sealing and coagulation of soft tissue and bone to address diffused bleeding during a surgical procedure.

One embodiment of the present disclosure provides a multifunction surgical instrument having a low-profile configuration to deliver both small vessel sealing through a bipolar clamping mechanism and transcollation sealing of diffused bleeding in a broad tissue plane, the multifunction surgical instrument including a reusable portion comprising a handle and an insertion portion, the insertion portion including a first jaw and a second jaw configured to transition between an open position and a closed position to serve as a clamp for sealing of tissue with a depth of up to about 7 mm, and a disposable electrode portion comprising a first conductive surface positioned in proximity to the first jaw and a second conductive surface positioned in proximity to the second jaw, the first and second conductive surfaces configured to emit a high-frequency alternating current sufficient to cause poaching of tissue clamped between the first and second jaws, and two or more electrodes and at least one saline port, wherein the two or more electrodes and the at least one saline port cooperate to affect transcollation sealing of diffused bleeding within a broad tissue plane.

In one embodiment, the handle of the reusable portion defines a pair of rings, each of the rings shaped and sized to enable a clinician to pass a finger therethrough for manipulation of the multifunction surgical instrument. In one embodiment, the reusable portion is constructed of a metallic based material configured to withstand the temperature and pressure of an autoclave for sterilization. In one embodiment, the first and second jaws are configured to produce a clamping pressure within a range of about 3 $kg/cm^2$ and about 16 $kg/cm^2$. In one embodiment, the disposable electrode portion further comprises a contact switch configured to automatically energize the first and second conductive surfaces upon application of a predefined quantity of pressure thereupon. In one embodiment, the first and second conductive surfaces are configured to emit a high frequency alternating current in the range of between about 200 kHz and about 3.3 MHz. In one embodiment, the multifunction surgical instrument further includes a blade configured to selectively transition distally-proximally along at least one of the first or second jaw. In one embodiment, the blade is actuated by a blade trigger.

In one embodiment, at least a first electrode is positioned adjacent to the first conductive surface and at least a second electrode is positioned adjacent to the second conductive surface. In one embodiment, at least one saline port is configured to deliver saline at a rate matched to radiofrequency energy emitted by the two or more electrodes. In one embodiment, activation of at least one saline port and two or more electrodes are affected by applying pressure to both a sealing button and a contact switch in the closed position. In one embodiment, the two or more electrodes and the at least one saline port are configured to produce hemostatic sealing within the surgical site at a temperature at or below 100° C. In one embodiment, the multifunction surgical instrument further includes a light emitting diode configured to at least partially illuminate a surgical site.

Another embodiment of the present disclosure provides a surgical instrument including a handle, a pair of jaws comprising a first jaw and a second jaw configured to transition between an open position and a closed position, a first conductive surface positioned in proximity to the first jaw and a second conductive surface positioned in proximity to the second jaw, the first and second conductive surfaces configured to emit a high-frequency alternating current sufficient to cause poaching of tissue clamped between the first and second jaws, and two or more electrodes and at least one saline port configured to affect transcollation sealing of diffused bleeding within a broad tissue plane.

Yet another embodiment of the present disclosure provides a multifunction surgical instrument having a low-profile configuration to deliver both small vessel sealing through a bipolar clamping mechanism and transcollation sealing of diffused bleeding in a broad tissue plane, the multifunction surgical instrument including a reusable portion, constructed of a metallic based material configured to withstand a temperature and pressure of an autoclave for sterilization, the reusable portion comprising a handle and an insertion portion, the insertion portion including a first jaw and a second jaw configured to transition between an open position and a closed position to serve as a clamp for sealing of vessels or tissue with a diameter or maximum dimensions of up to about 7 mm, and wherein the handle of the reusable portion defines a pair of rings, each of the rings shaped and sized to enable a clinician to pass a finger therethrough for manipulation of the multifunction surgical instrument, a disposable electrode portion comprising a first conductive surface positioned in proximity to the first jaw and a second conductive surface positioned in proximity to the second jaw, the first and second conductive surfaces configured to emit a high-frequency alternating current sufficient to cause poaching of tissue clamped between the first and second jaws, a contact switch configured to automatically energize the first and second conductive surfaces upon application of a predefined quantity of pressure thereupon, a blade configured to selectively transition distally-proximally along at least one of the first or second jaws, and two or more electrodes and at least one saline port, wherein the two or more electrodes and the at least one saline port cooperate to affect transcollation sealing of diffused bleeding within a broad tissue plane, wherein activation of the at least one saline port and the two or more electrodes are affected by applying pressure to both a sealing button and a contact switch in the closed position.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which:

FIG. 6A is a close-up perspective view depicting the multifunction surgical instrument with clamping jaws clamped around a bundle of tissue within a surgical site, in accordance with an embodiment of the disclosure.

FIG. 6B is a close-up perspective view depicting the multifunction surgical instrument of FIG. 6A emitting high-frequency alternating current to the bundle of tissue, in accordance with an embodiment of the disclosure.

FIG. 6C is a close-up perspective view depicting the multifunction surgical instrument of FIG. 6B upon release of the bundle of tissue, in accordance with an embodiment of the disclosure.

Figure 1:
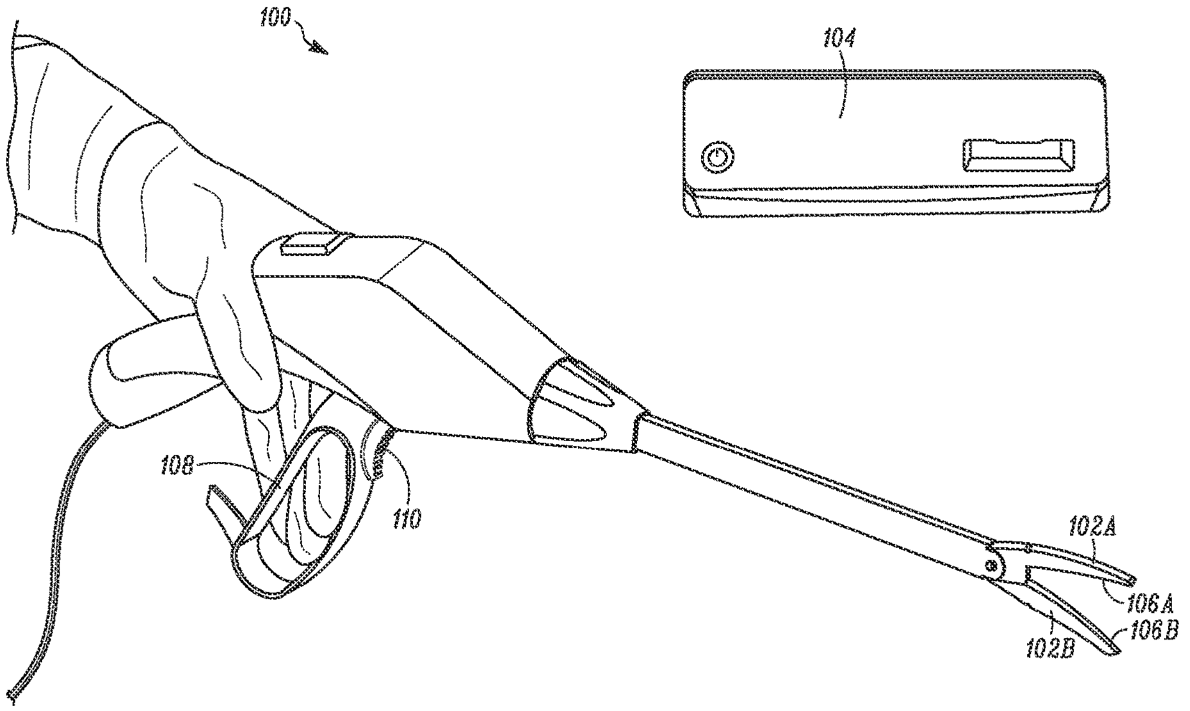
FIG. 1 (PRIOR ART)
FIG. 1 is a perspective view depicting a conventional bipolar vessel sealing device, in accordance with the prior art.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

As a general matter, reducing the number of tools or instruments that are used simultaneously during a surgical procedure is beneficial because each instrument obstructs access to the surgical site in some way, or requires a larger incision that would otherwise be required to provide access for the other instruments needed to perform the procedure. One solution to this problem is to change specialized tools throughout the procedure such that there are a limited number involved in the procedure at any given time. Changing tools, however, is a process that can present its own challenges.

Figure 3A:
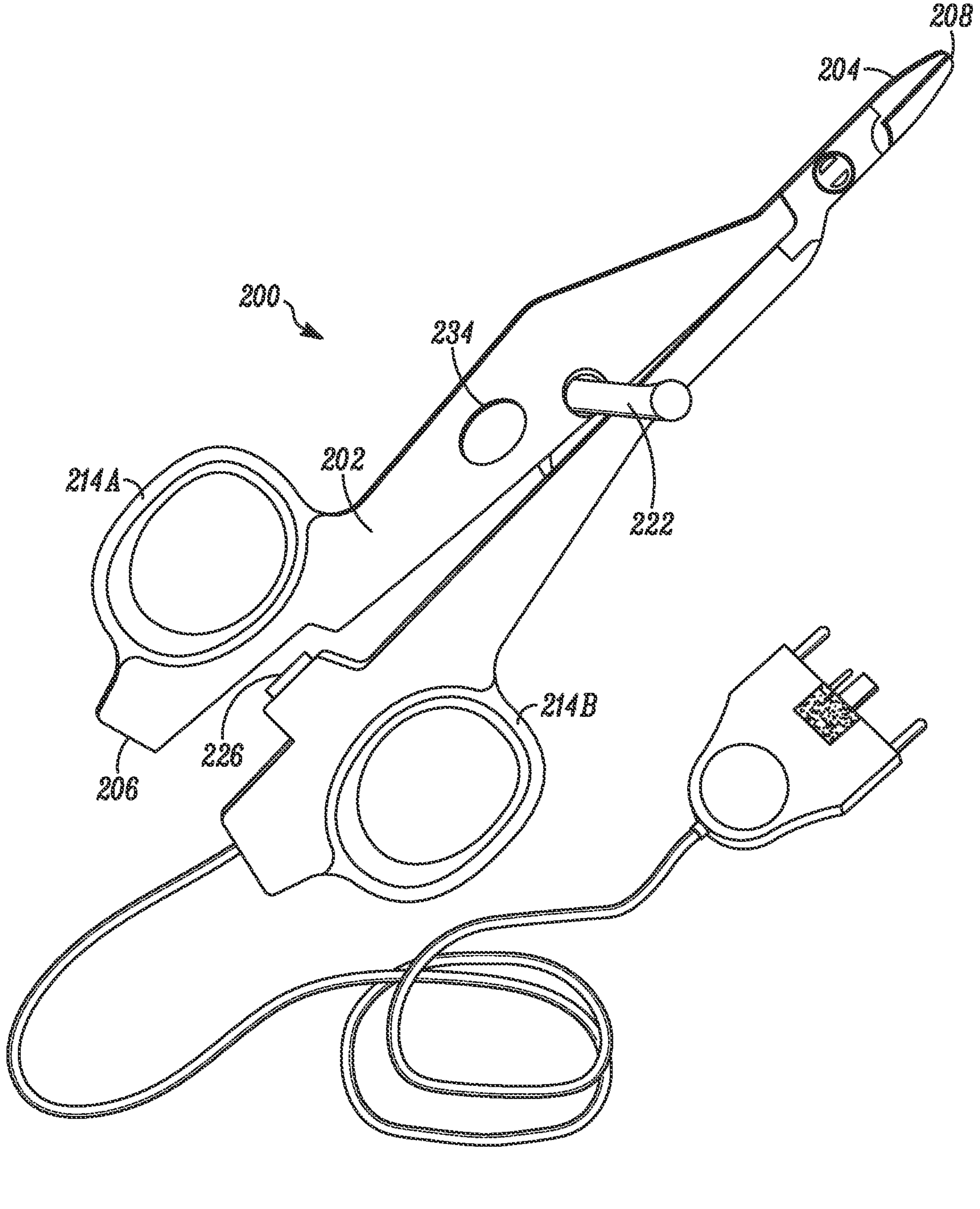
FIG. 3A is a profile view depicting a disposable multifunction surgical instrument having a low-profile configuration to deliver both small vessel sealing through a bipolar clamping mechanism and transcollation sealing of diffused bleeding in a broad tissue plane, in accordance with an embodiment of the disclosure.

As described herein, use of a single, multi-function device or instrument provides both clamping and small-vessel (e.g., diameters of between about 1 mm and about 2 mm, and in some cases up to a diameter of about 7 mm, etc.) sealing and coagulation of diffused bleeding without the need for instrument changes or a larger incision. Referring to FIG. 3A, a multifunction surgical instrument 200 having a low-profile, ring handle configured to deliver both vessel dissection and sealing through a bipolar clamping mechanism and a combination of bipolar radiofrequency energy and saline to provide hemostatic sealing and coagulation of soft tissue and bone to address diffused bleeding during a surgical procedure is depicted in accordance with an embodiment of the disclosure. As depicted, the instrument 200 can include a handle 202 and an insertion portion 204. The insertion portion 204 can extend from a proximal end 206 near the handle 202 to a distal end 208 configured to define a therapeutic effect, such as sealing, clamping or coagulation of diffused bleeding at a surgical site.

As used herein, the term "distal" refers to the portion of the instrument or component thereof that is being described that is further from a clinician or user, while the term "proximal" refers to the portion of the instrument or component thereof that is being described that is closer to a clinician or user. Further, to the extent consistent, any of the aspects described herein may be used in conjunction with any of the other aspects described herein. As used herein the term "tissue" is meant to include variously-sized vessels and broad planes of biological matter.

Further, it is to be appreciated that the term "clinician" refers to any individual configured to use or manipulate example embodiments described herein or alternative combinations thereof during a procedure. Similarly, the term "patient" or "subject," as used herein is to be understood to refer to an individual or object in which the use of the device is to occur during a procedure, whether human, animal, or inanimate. Various descriptions are made herein, for the sake of convenience, with respect to the procedures being performed by a clinician on a patient or subject (the involved parties collectively referred to as a "user" or "users") while the disclosure is not limited in this respect.

Figure 4A:
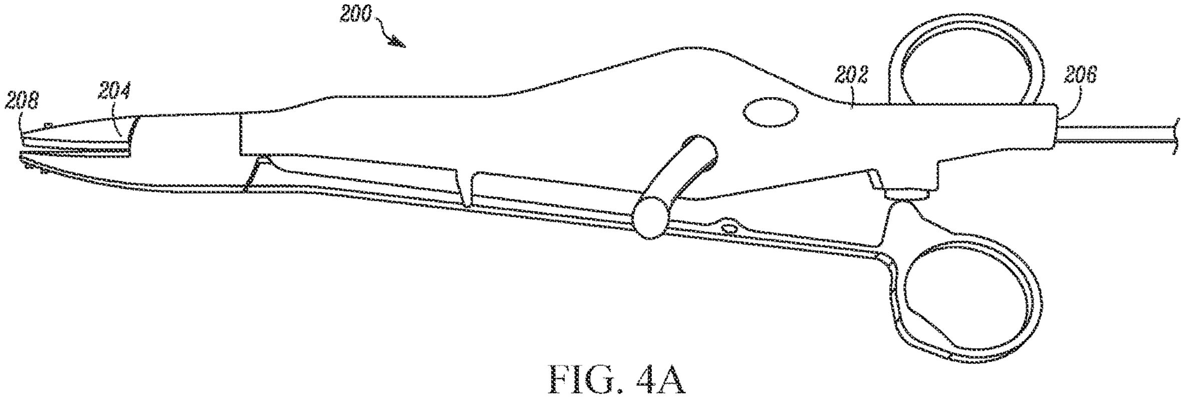
FIG. 4A is a profile view depicting a reposable multifunction surgical instrument having a low-profile configuration to deliver both small vessel sealing through a bipolar clamping mechanism and transcollation sealing of diffused bleeding in a broad tissue plane, in accordance with an embodiment of the disclosure.

In some embodiments, the multifunction surgical instrument 200 can be disposable, in that the entire handpiece is considered a consumable item to be disposed of at the conclusion of a surgical procedure. In other embodiments, the multifunction surgical instrument 200 can be reposeable, in that at least one portion of the instrument 200 is reusable, while other portions of the instrument 200 are disposable. For example, with reference to FIGS. 4A-B, the multifunction surgical instrument 200 can include a reusable clamp portion 210 and a disposable electrode portion 212 configured to minimize waste, particularly when compared to a single use device. In some embodiments, the reusable clamp portion 210 can be constructed of a material (e.g., a metal or metal alloy) configured to withstand the temperature and pressure of an autoclave and/or generally be unreacted of when submerged in a chemical bath for sterilization. Various embodiments of the present invention will be described in detail with reference to the drawings, wherein like reference numerals represent like parts and assemblies throughout the several views.

Figure 2:
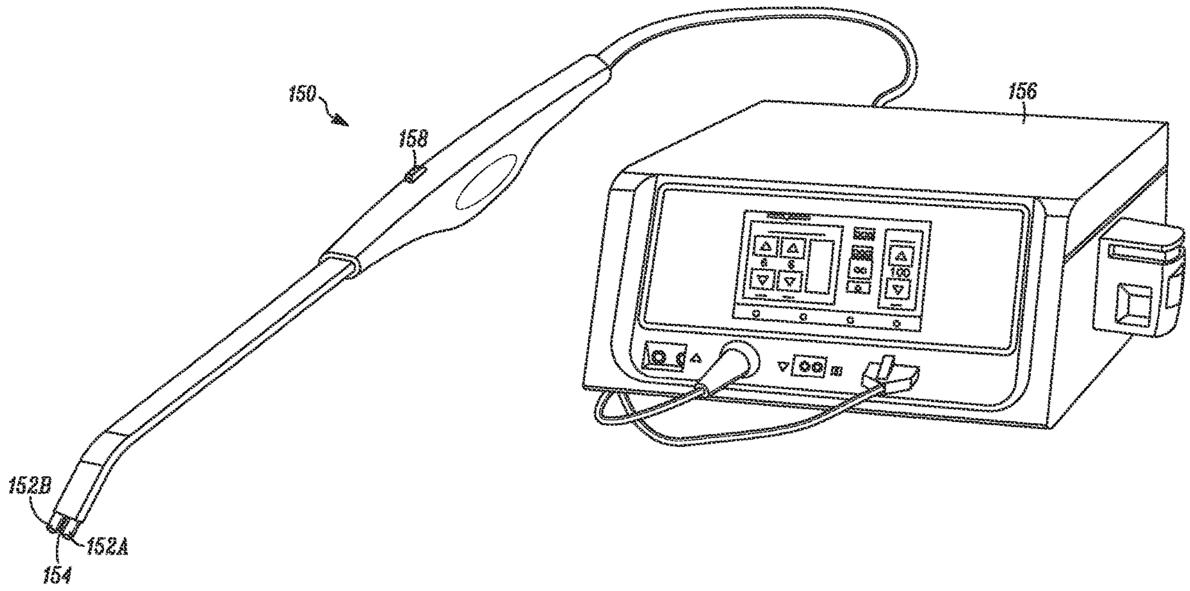
FIG. 2 (PRIOR ART)
FIG. 2 is a perspective view depicting a transcollation sealing device, in accordance with the prior art.
Figure 4B:
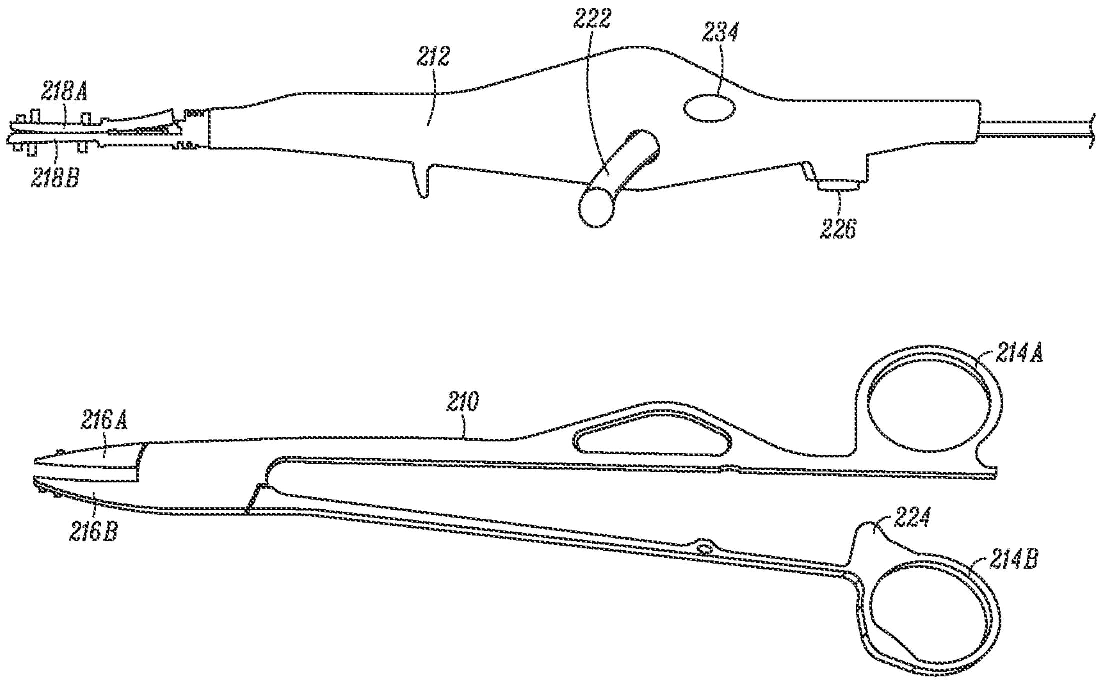
FIG. 4B is an exploded, profile view depicting the multifunction surgical instrument of FIG. 4A.

With continued reference to FIGS. 3A and 4B, in embodiments, the handle portion 202 can include a pair of rings 214A/B, generally shaped and sized to have the haptic qualities of a hemostat, thereby providing a familiarity to clinicians even without previous experience. For example, in one embodiment, the pair of rings 214A/B can present openings measuring between about 0.75 inches and about 2 inches, thereby enabling a user or clinician to pass a finger therethrough for manipulation of the instrument 200. Moreover, the pair of rings 214A/B can present in easy to manipulate, low-profile alternative to traditional pistol grip designs (such as that depicted in FIGS. 1 and 2). Accordingly, embodiments of the present disclosure present a single, multifunction, low-profile instrument 200 designed to reduce visual obstruction during a surgical procedure, as well as to emulate the haptic qualities of a hemostat, scissors or other familiar surgical instrument.

Figure 3B:
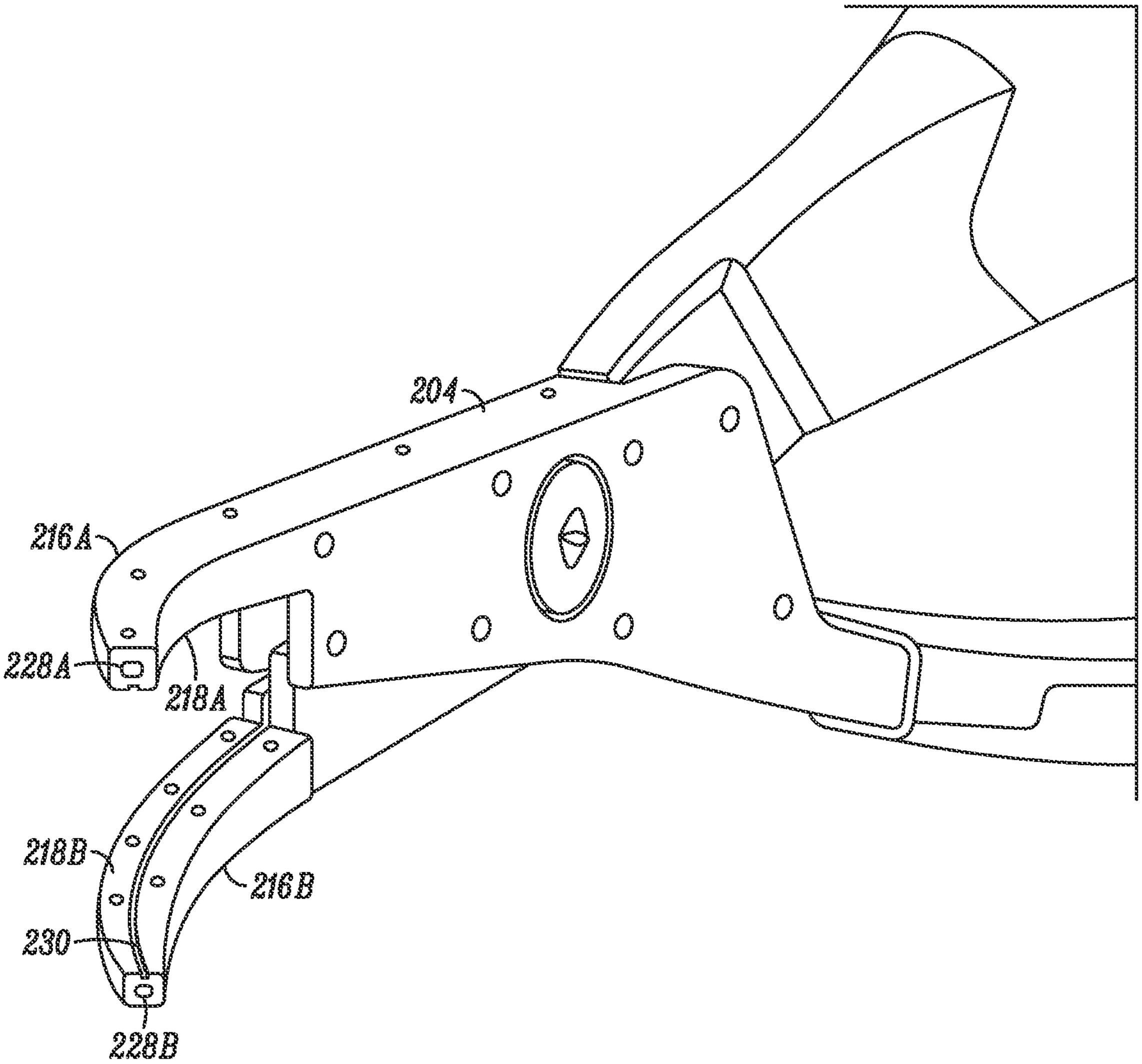
FIG. 3B is a close-up, perspective view depicting clamping jaws of a multifunction surgical instrument, in accordance with an embodiment of the disclosure.

With additional reference to FIG. 3B, in embodiments, the insertion portion 204 can define a pair of jaws 216A/B, each of which can include a conductive surface 218A/B, with each surface 218A/B representing an electrical pole. In reposeable embodiments (e.g., as depicted in FIG. 4B), the pair of jaws 216A/B can be represented by both the reusable clamp portion 210 and the disposable electrode portion 212, while the conductive surfaces 218A/B are represented solely by the disposable electrode portion 212. In embodiments, the pair of jaws 216A/B and conductive surfaces 218A/B can transition between a closed position (as depicted in FIG. 3A) and an open position (as depicted in FIG. 3B).

Figure 5A:
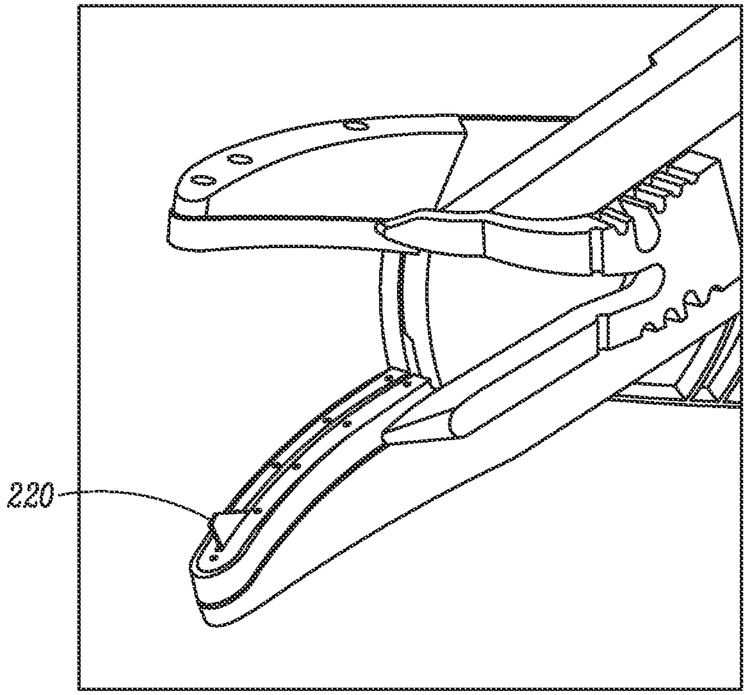
FIG. 5A is a close-up, perspective view depicting clamping jaws of a multifunction surgical instrument including a sliding blade, in accordance with an embodiment of the disclosure.
Figure 5B:
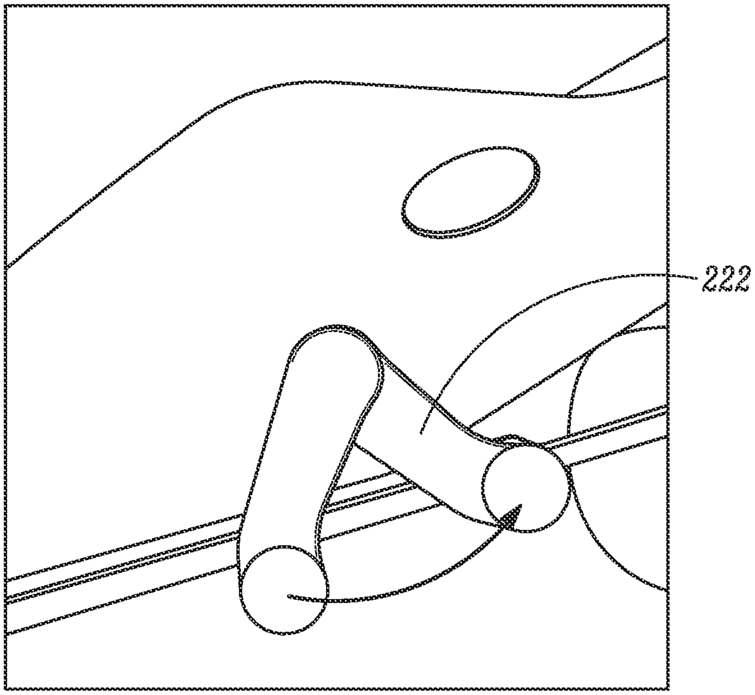
FIG. 5B is a close-up, perspective view depicting a multifunction surgical instrument including a blade actuator trigger, in accordance with an embodiment of the disclosure.

With additional reference to FIG. 5A, in some embodiments, at least one of the jaws 216A/B can further include a blade 220, which can be configured to slide or otherwise transition distally and conversely proximally along the jaw 216, thereby enabling a smoother cut when sealing and dividing blood vessels or other tissue structures. To facilitate manipulation of the blade 220, in some embodiments, the instrument 200 can include a blade trigger 222 located on the handle portion 202 of the instrument 200. Accordingly, an applied pressure or other movement of the blade trigger 222 can affect corresponding movement of the blade 220.

Figure 5C:
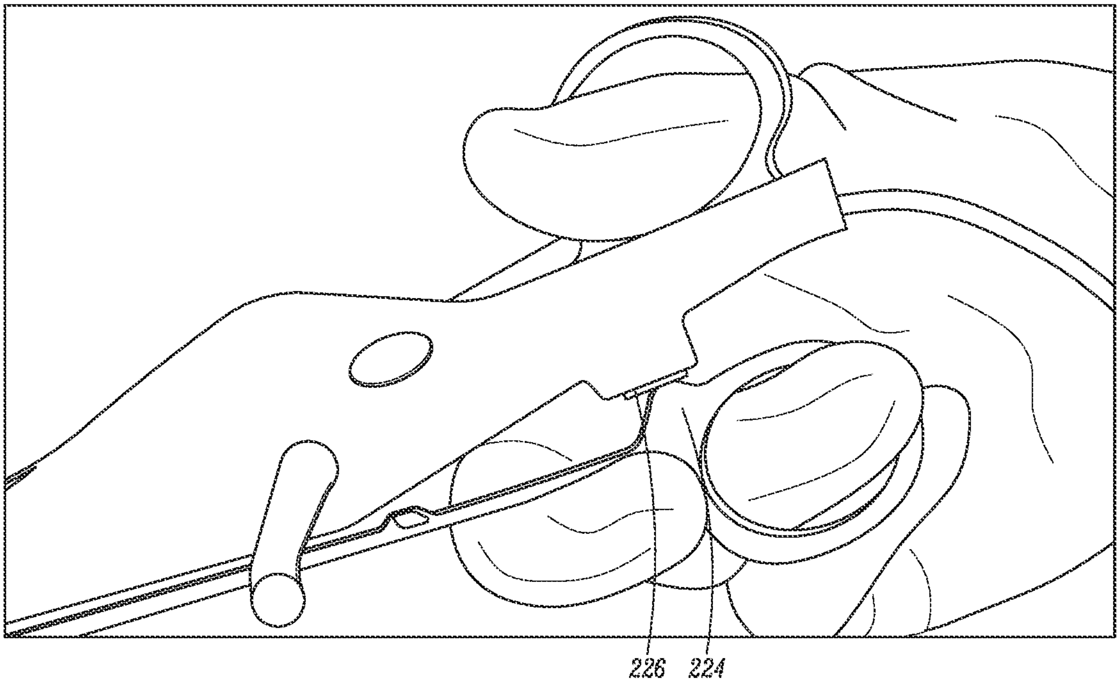
FIG. 5C is a close-up, perspective view depicting a multifunction surgical instrument including a contact switch configured to automatically energize a first and second pole of bipolar contacts upon transitioning of clamping jaws of the multifunction surgical instrument to a closed position, in accordance with an embodiment of the disclosure.

With additional reference to FIG. 5C, in some embodiments the handle portion 202 can include a projection 224 or other surface configured to make contact with a contact switch 226, thereby selectively energizing the conductive surfaces 218A/B with a supply of radiofrequency energy. In some embodiments, the contact switch 226 can be a two-stage switch, having a first stage activated in the closed position below a defined clamping pressure threshold, and a second stage activated in the closed position above a defined clamping pressure threshold. Accordingly, in some embodiments, application of a defined clamping force upon the handle 202 (e.g., when clamping tissue between the jaws 216A/B) can automatically activate bipolar sealing of the clamping mechanism when the contact switch 226 is in the second stage of activation. For example, in some embodiments, a defined clamping pressure of the jaws 216A/B within the range of about 3 $kg/cm^2$ and about 16 $kg/cm^2$ can be sufficient to automatically activate the conductive surfaces 218A/B with radiofrequency energy; although other methods of activation are also contemplated.

Accordingly, as depicted in FIG. 6A, when operating in the bipolar clamping dissection and sealing mode, sealing of small vessels of up to about 1-2 mm, and in some embodiments up to about 7 mm in diameter, can be affected by positioning the vessel or tissue within the jaws 216A/B of the instrument 200 and applying a clamping force by squeezing on the handle 202, thereby closing the jaws 216A/B and energizing be conductive surfaces 218A/B. As depicted in FIG. 6B, a high-frequency alternating current causes hydrated tissue clamped between the jaws 216A/B to heat up, which in turn causes the native tissue proteins to denature (sometimes referred to as “poaching”), while water turns to vapor and escapes. The high-frequency alternating current fuses the intimal walls of the vessel or tissue, resulting in complete lumen occlusion. Thereafter, the blade 220 can be manipulated (e.g., via trigger 224) to affect a physical separation of the lumen.

In some embodiments, an energy generator can provide radiofrequency controlled by an advanced algorithm for optimal tissue sealing. For example, in some embodiments, the conductive surfaces 218A/B can be configured to emit a high-frequency electrical current (e.g., between about 200 kHz to about 3.3 MHz), or other frequency above a range that would tend to cause nerve or muscle stimulation. In some embodiments, the conductive surfaces 218A/B can be configured to monitor an electrical resistance of the tissue to determine exactly how much radiofrequency energy is needed to affect sealing. Further, in some embodiments, at least one of the jaws 216A/B and/or conductive surfaces 218A/B can include a nonstick coating, for example in the form of a thin polymer, resulting in easier separation of the jaws 216A/B from the tissue (nonstick), less eschar at the surgical site, and with a decreased buildup of charred tissue on the instrument 200.

In addition to clamping and sealing of vessels, in embodiments, the instrument 200 can also employ transcollation technology for coagulation of diffused bleeding, thereby reducing the need for multiple instruments or exchange of instruments during a surgical procedure. For example, with additional reference to FIG. 7, in embodiments, the instrument 200 can include two or more electrodes 228A/B and at least one saline port 230 as a mechanism for affecting transcollation sealing.

Figure 7:
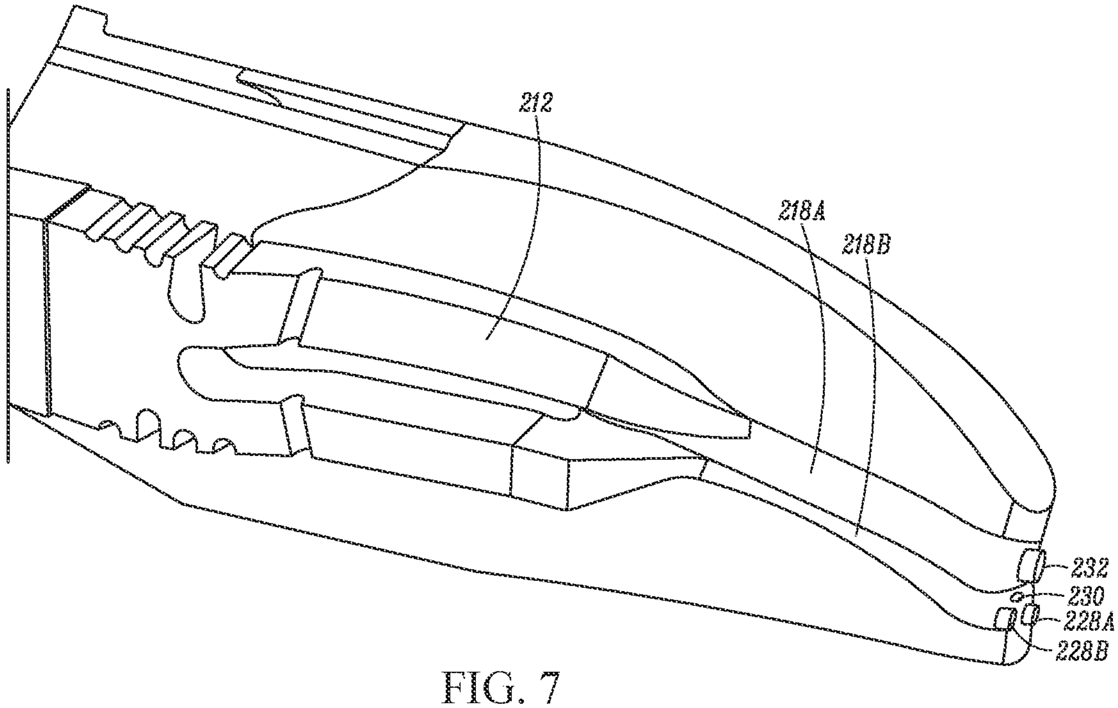
FIG. 7 is a close-up perspective view depicting a multi-function surgical instrument having a mechanism configured to apply transcollation technology for coagulation of diffused bleeding within a broad tissue plane, in accordance with an embodiment of the disclosure.
Figure 8:
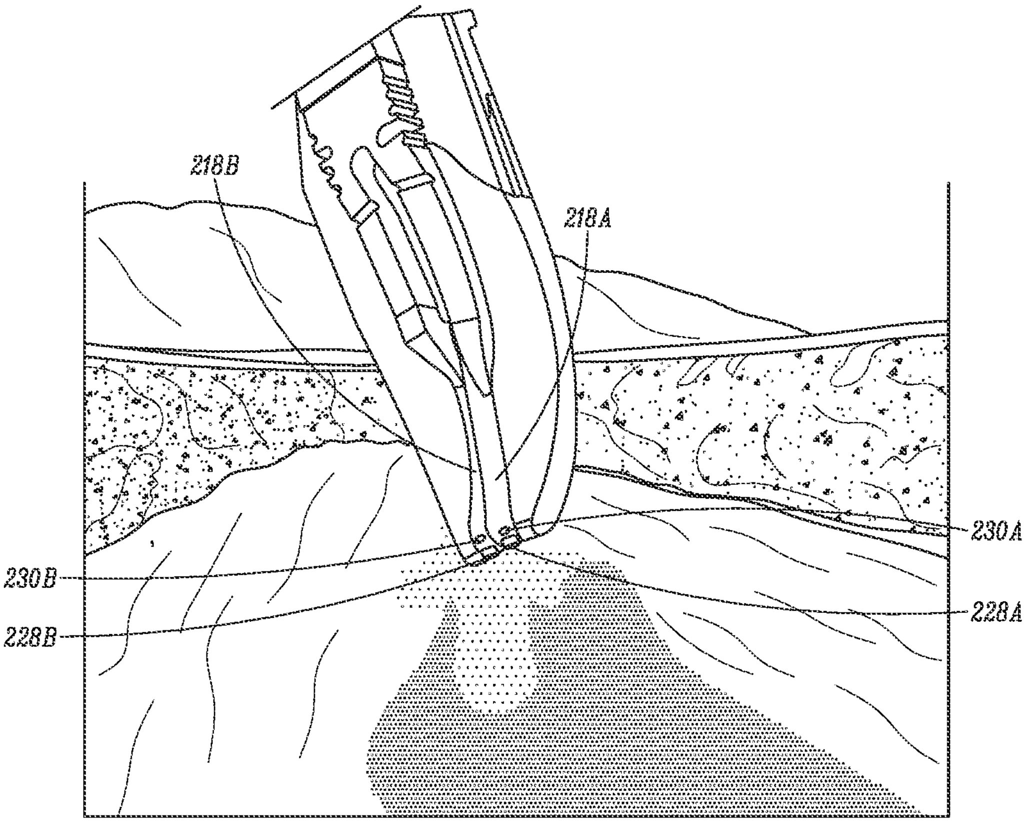
FIG. 8 is a close-up perspective view depicting a multi-function surgical instrument applying transcollation technology to a broad tissue plane, in accordance with an embodiment of the disclosure.

In the disposable embodiment (as depicted in FIG. 3B), the two or more electrodes 228A/B and saline port 230 can be positioned in proximity to the distal and 208 of the insertion portion 204. In the reposable embodiment (as depicted in FIG. 7), the two or more electrodes 228A/B can be positioned on the disposable electrode portion 212, for example adjacent to one of the conductive surfaces 218A/B. For example, in one embodiment, a pair of electrodes 228A/B and a saline port 230 are positioned adjacent to the lower conductive surface 218B. In other embodiments, such as that depicted in FIGS. 3B and 8, a first electrode 228A can be positioned adjacent to a first conductive surface 218A, while a second electrode 228B can be positioned adjacent to a second electrode surface 218B. Similarly, at least one saline port 230A can be positioned adjacent to the first electrode 228A and a second optional saline port 230B can be positioned adjacent to the second electrode 228B (as depicted in FIG. 8). Other combinations and configurations of electrode 228A/B and saline port 230 positions are also contemplated. Further, in some embodiments, the instrument 200 can include one or more light sources 232 (e.g., light emitting diodes or the like) configured to selectively aid in illumination of the surgical site (as depicted in FIG. 7).

Accordingly, with reference to FIG. 8, when diffused hemostatic sealing is desired, a clinician can depress the transcollation sealing button 234 located on the handle portion 202 (as depicted in FIG. 3A) or on a body of the disposable electrode portion 212 (as depicted in FIG. 4B). In other embodiments, diffused hemostatic sealing can require both a combination of applied pressure to both the sealing button 234 and the contact switch 226 (e.g., positioning of the contact switch in the first stage of activation). Thus, in some embodiments, the instrument 200 must be in the closed position (e.g., wherein the jaws 216A/B are in close proximity to one another) to enable transcollation. In other embodiments, transcollation can be affected through a range of instrument 200 configurations (e.g., between a closed position and the open position), thereby enabling transcollation over a variable distance between the first and second electrodes 228A/B to affect greater control over tissue desiccation.

In some embodiments, a distance between the first and second electrodes 228A/B can be affected through manipulation of the handle rings 214A/B, thereby enabling medical personnel to selectively control an intensity and/or depth of the electrosurgical effect of the electrodes 228A/B. For example, a surgeon may establish a fixed distance between the electrodes 228A/B while manipulating the entire instrument 200, bringing the electrodes 228A/B into, and out of, contact with tissue to work the surgical site. In another example, a surgeon may bring the electrodes 228A/B into substantially continuous contact with tissue, and manipulate a distance between the electrodes 228A/B. In some embodiments, a distance between the electrodes 228A/B can be sensed by the contact switch 226 (e.g., pressure switch, etc.), which in communication with a system pump generator can dictate the magnitude of energy transmitted to the electrodes 228A/B and volume of saline delivered to the port 230.

Thereafter, a combination of radiofrequency energy provided by the electrodes 228A/B and saline provided by the one or more saline ports 230 can affect low temperature hemostasis to affect collation and general sealing within a broad tissue plane. Specifically, saline, or some other fluid or fluid like substance (e.g., deionized water, glycol, etc.) that is both a good conductor of electricity and not damaging to the surrounding tissues and structures, can be introduced into the surgical site by one or more saline ports 230, while the electrodes 228A/B provide electrical current sufficient to poach the bathed region. In this manner the one or more ports 230 deliver saline at a rate matched to the radiofrequency energy emitted by the electrodes 228A/B.

Thereafter, electrosurgical energy flows between the electrodes 228A/B forming a radiating pattern, which radiates between the electrodes 228A/B. In embodiments, manipulation of the handle rings 214A/B enables a clinician to apply transcollation technology to the surgical site with the painting motion to seal broad tissue planes, to spot treat bleeding vessels up to about 1 mm in diameter, as well as to treat bleeding vessels that have retracted into surrounding tissue that cannot be easily grasped by the jaws 216A/B. In some embodiments, the transcollation technology can be configured to produce hemostatic sealing without burning, char or smoke, wherein the presence of saline maintains temperatures within the surgical site at or below about 100° C.

Accordingly, embodiments of the present disclosure enable clamping and small vessel sealing, as well as coagulation of diffused bleeding within a tissue plane without a need for instrument changes or a larger incision, thus resulting in improved visibility for clinicians, shorter surgical procedure times, and improved patient outcomes (e.g., faster recovery rates, greater hemoglobin retention, etc.). With its ability to clamp vessels and other tissues for bipolar dissection and sealing, as well as to provide transcoalition of broad tissue planes, the multifunction surgical instruments 200 of the present disclosure are particularly adept at surgeries which otherwise require multiple instruments, including for example, solid organ resection, spinal surgery, trauma procedures, an orthopedic reconstruction of the hip and knee, just to name a few.

Moreover, embodiments of the present disclosure, employ a low-profile ring handle configuration with a form factor similar to a hemostatic or other instrument which surgeons are accustomed. Accordingly, in addition to reduced surgical times, reduced cost, higher hemoglobin retention for the patient, and reductions in postsurgical blood loss, embodiments of the present disclosure provide improved visibility of the surgical site, as well as a haptic familiarity to surgeons, particularly in comparison to pistol grip handle designs (such as that depicted in FIGS. 1 and 2).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical instrument comprising:

a handle;

a pair of jaws comprising a first jaw and a second jaw configured to transition between an open position and a closed position;

a first conductive surface positioned in proximity to the first jaw and a second conductive surface positioned in proximity to the second jaw, the first conductive surface and the second conductive surface configured to emit a high-frequency alternating current sufficient to cause poaching of tissue clamped between the first jaw and the second jaw;

two or more electrodes and at least one saline port at a distal end of the instrument, configured to affect transcollation sealing of diffused bleeding within a broad tissue plane, wherein each conductive surface includes an exposed channel for directing saline to the distal end, such that the saline port is formed by the jaws being in the closed position, wherein a first of the two or more electrodes is positioned adjacent to the first conductive surface and a second of the two or more electrodes is positioned adjacent to the second conductive surface; and a contact switch configured to sense a distance between the first of the two or more electrodes and the second of the two or more electrodes, wherein the contact switch comprises a two-stage switch having a first stage activated in the closed position below a defined clamping pressure threshold and a second stage activated in the closed position above the defined clamping pressure threshold, wherein the handle defines a pair of rings, each of the rings shaped and sized to enable a clinician to pass a finger therethrough for manipulation of the multifunction surgical instrument, wherein the contact switch is arranged on one of the rings, and further wherein the other of the rings includes a projection configured to make contact with the contact switch during operation of the instrument.

2. The surgical instrument of claim 1, wherein the pair of jaws are configured to serve as a clamp for sealing of vessels with a diameter of up to about 7 mm.

3. The surgical instrument of claim 1, further comprising a blade configured to selectively transition distally-proximally along at least one of the first jaw or the second jaw.

4. The surgical instrument of claim 3, wherein the blade is actuated by a blade trigger.

5. The surgical instrument of claim 1, wherein activation of the at least one saline port and the two or more electrodes are affected by applying pressure to a sealing button.

6. The surgical instrument of claim 1, wherein a distance between the two or more electrodes is variable during transcollation sealing.

7. The surgical instrument of claim 1, wherein in the first stage the first of the two or more electrodes and the second of the two or more electrodes are energized for transcollation sealing of diffused bleeding within the tissue that is not positioned between the pair of jaws, and in the second stage the first conductive surface and the second conductive surface are energized for poaching of tissue clamped between the pair of jaws.

8. The surgical instrument of claim 1, further comprising a light emitting diode configured to at least partially illuminate a surgical site.

9. A multifunction surgical instrument having a low-profile configuration to deliver both small vessel sealing through a bipolar clamping mechanism and transcollation sealing of diffused bleeding in a broad tissue plane, the multifunction surgical instrument comprising:

a handle and an insertion portion, the insertion portion including a first jaw and a second jaw configured to transition between an open position and a closed position to serve as a clamp for sealing of vessels with a diameter of up to about 7 mm; and a first conductive surface positioned in proximity to the first jaw and a second conductive surface positioned in proximity to the second jaw, the first conductive surface and the second conductive surface configured to emit a high-frequency alternating current sufficient to cause poaching of tissue clamped between the first jaw and the second jaw; and two or more electrodes and at least one saline port at a distal end of the instrument, wherein the two or more electrodes and the at least one saline port cooperate to affect transcollation sealing of diffused bleeding within a broad tissue plane, wherein each conductive surface includes an exposed channel for directing saline to the distal end, such that the saline port is formed by the jaws being in the closed position, wherein a first of the two or more electrodes is positioned adjacent to the first conductive surface and a second of the two or more electrodes is positioned adjacent to the second conductive surface; and a contact switch configured to sense a distance between the first of the two or more electrodes and the second of the two or more electrodes, wherein the contact switch comprises a two-stage switch having a first stage activated in the closed position below a defined clamping pressure threshold and a second stage activated in the closed position above a defined clamping pressure threshold, wherein the handle defines a pair of rings, each of the rings shaped and sized to enable a clinician to pass a finger therethrough for manipulation of the multifunction surgical instrument, wherein the contact switch is arranged on one of the rings, and further wherein the other of the rings includes a projection configured to make contact with the contact switch during operation of the instrument.

10. The multifunction surgical instrument of claim 9, wherein the handle comprises a reusable portion, and the first conductive surface, the second conductive surface, and the two or more electrodes comprise a disposable portion.

11. The multifunction surgical instrument of claim 10, wherein the reusable portion is constructed of a metallic based material configured to withstand a temperature and pressure of an autoclave for sterilization.

12. The multifunction surgical instrument of claim 10, wherein the contact switch is further configured to automatically energize the first conductive surface and the second conductive surface upon application of a defined quantity of pressure thereupon.

13. The multifunction surgical instrument of claim 9, wherein the first jaw and the second jaw are configured to produce a clamping pressure within a range of about 3 $kg/cm^2$ and about 16 $kg/cm^2$.

14. The multifunction surgical instrument of claim 9, wherein the first conductive surface and second conductive surface are configured to emit a high frequency alternating current in the range of between about 200 kHz and about 3.3 MHz.

15. The multifunction surgical instrument of claim 9, further comprising a blade configured to selectively transition distally-proximally along at least one of the first jaw or the second jaw.

16. The multifunction surgical instrument of claim 15, wherein the blade is actuated by a blade trigger.

17. The multifunction surgical instrument of claim 9, wherein the two or more electrodes and the at least one saline port are configured to produce hemostatic sealing within the surgical site at a temperature at or below 100° C.

18. A multifunction surgical instrument having a low-profile configuration to deliver both small vessel sealing through a bipolar clamping mechanism and transcollation sealing of diffused bleeding in a broad tissue plane, the multifunction surgical instrument comprising:

a handle defining a pair of rings shaped and sized to enable a clinician to pass a finger therethrough for manipulation of the multifunction surgical instrument;

an insertion portion including a first jaw and a second jaw configured to transition between an open position and a closed position to serve as a clamp for sealing of tissue with a depth of up to about 7 mm;

a first conductive surface positioned in proximity to the first jaw and a second conductive surface positioned in proximity to the second jaw, the first conductive surface and the second conductive surface configured to emit a high-frequency alternating current sufficient to cause poaching of tissue clamped between the first jaw and the second jaw;

a contact switch configured to automatically energize the first conductive surface and second conductive surface upon application of a defined quantity of pressure thereupon;

a blade configured to selectively transition distally-proximally along at least one of the first jaw or the second jaw; and two or more electrodes and at least one saline port at a distal end of the instrument, wherein the two or more electrodes and the at least one saline port cooperate to affect transcollation sealing of diffused bleeding within a broad tissue plane, wherein each conductive surface includes an exposed channel for directing saline to the distal end, such that the saline port is formed by the jaws being in the closed position, wherein a first of the two or more electrodes is positioned adjacent to the first conductive surface and a second of the two or more electrodes is positioned adjacent to the second conductive surface, wherein each of the pair of rings is shaped and sized to enable a clinician to pass a finger therethrough for manipulation of the multifunction surgical instrument, wherein the contact switch is arranged on one of the rings, and further wherein the other of the rings includes a projection configured to make contact with the contact switch during operation of the instrument.

* * * * *